(12) United States Patent
Xiang et al.

(10) Patent No.: US 10,280,460 B2
(45) Date of Patent: May 7, 2019

(54) **DNA PROBE SEQUENCE FOR GENETIC SEX IDENTIFICATION OF *LITOPENAEUS VANNAMEI* AND ACQUISITION METHOD**

(71) Applicant: INSTITUTE OF OCEANOLOGY, CHINESE ACADEMY OF SCIENCES, Shandong (CN)

(72) Inventors: Jianhai Xiang, Shandong (CN); Yang Yu, Shandong (CN); Fuhua Li, Shandong (CN); Xiaojun Zhang, Shandong (CN)

(73) Assignee: INSTITUTE OF OCEANOLOGY, CHINESE ACADEMY OF SCIENCES, Shandong (CN)

( * ) Notice: Subject to any disclaimer, the term of this patent is extended or adjusted under 35 U.S.C. 154(b) by 98 days.

(21) Appl. No.: 15/322,307

(22) PCT Filed: Dec. 4, 2015

(86) PCT No.: PCT/CN2015/096369
§ 371 (c)(1),
(2) Date: Dec. 27, 2016

(87) PCT Pub. No.: WO2016/180009
PCT Pub. Date: Nov. 17, 2016

(65) Prior Publication Data
US 2017/0175188 A1 Jun. 22, 2017

(30) Foreign Application Priority Data
May 14, 2015 (CN) .......................... 2015 1 0245304

(51) Int. Cl.
*C07H 21/04* (2006.01)
*C12Q 1/68* (2018.01)
*C12Q 1/6879* (2018.01)

(52) U.S. Cl.
CPC ..... *C12Q 1/6879* (2013.01); *C12Q 2600/158* (2013.01)

(58) Field of Classification Search
None
See application file for complete search history.

(56) References Cited

U.S. PATENT DOCUMENTS 8,258,281 B2   9/2012   Vuylsteke et al.

FOREIGN PATENT DOCUMENTS

| CN | 101432442 A | 5/2009 |
| CN | 101709332 A | 5/2010 |
| CN | 104789690 A | 7/2015 |

OTHER PUBLICATIONS

International Search Report for PCT/CN2015/096369, dated Feb. 29, 2016 in English and Chinese Language.
Staelens, J., et al. High-density linkage maps and sex-linked markers for the black tiger shrimp (*Penaeus monodon*).Genetics, 2008, 179(2): pp. 917-925.
Zhang, L., et al. A genetic linkage map of Pacific white shrimp (*Litopenaeus varmamei*): sex-linked microsatellite markers and high recombination rates. Genetica, 2006, 131(1): pp. 37-49.
Alcivar-Warren, A., et al. ShrimpMap: A low-density, microsatellite-based linkage map of the pacific whiteleg shrimp, Litopenaeus vannamei: Identification of sex-linked markers in linkage group 4. Journal of Shellfish Research, 2007, 26(4): pp. 1259-1277.
Li, Z., et al. AFLP-based genetic linkage map of marine shrimp Penaeus (*Fenneropenaeus*) chinensis. Aquaculture, 2006, 261(2): pp. 463-472.
Sun, Z., et al. Construction of a genetic linkage map in fenneropenaeus chinensis (Osbeck) using RAPD and SSR markers. Hydrobioloaia, 2008,596: pp. 133-141.
Liu, B., et al. A genetic linkage map of marine shrimp Penaeus (*Fenneropenaeus*) chinensis based on AFLP, SSR, and RAPD markers. Chinese Journal of Oceanology and Limnology, 2010, 28(4): pp. 815-825.
Li, S., et al. Screening of Genes Specifically Expressed in Males of Fenneropenaeus, chinensis and Their Potential as Sex Markers. Journal of Marine Biology, 2013, pp. 1-9.
Written Opinion of the International Search Authority dated Feb. 29, 2016 for International Patent Application No. PCT/CN2015/096369 (4 pages in Chinese with English Translation).
International Preliminary Report on Patentability dated Nov. 14, 2017 for International Patent Application No. PCT/CN2015/096369 (5 pages in Chinese with English Translation).

(Continued)

*Primary Examiner* — Jeanine A Goldberg
(74) *Attorney, Agent, or Firm* — Smith, Gambrell & Russell, LLP

(57) ABSTRACT

The present invention relates to a DNA sequence showing difference between the female and male individuals of *Litopenaeus vannamei* and its corresponding acquired method. The method comprises: respectively conducting high-through put sequencing on the mixing pools of female individuals and male individuals in by high-through put sequencing platform; conducting bioinformatic analysis on the sequencing results to screen out sequences showing significant difference between the mixing pools of female and male individuals; verifying the obtained sex difference sequence in individuals from different sources; and finally, obtaining a probe sequence for female and male identification of *L. vannamei*, so that the genetic sex of this species can be accurately identified using the sequences. The method of the present invention has the characteristics of high efficiency, accuracy and reliability, and possess broad application potential in the early sex identification and sex control research of prawns.

5 Claims, No Drawings
Specification includes a Sequence Listing.

(56) References Cited

OTHER PUBLICATIONS

Chinese Search Report for Chinese Patent Application No. 201510245304.9 dated Jun. 20, 2016 (1 page).
Chinese First Office Action for Chinese Patent Application No. 201510245304.9 dated Jun. 23, 2016 (3 pages in Chinese with English Translation).

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: LvSDPF primer

<400> SEQUENCE: 1
ccagacagaa atgatctcct ttga        24

<210> SEQ ID NO 2
<211> LENGTH: 24
<212> TYPE: DNA
<213> ORGANISM: Artificial Sequence
<220> FEATURE:
<223> OTHER INFORMATION: LvSDPR primer

<400> SEQUENCE: 2
agaaaagaaa agaggaaagc agga        24

<210> SEQ ID NO 3
<211> LENGTH: 513
<212> TYPE: DNA
<213> ORGANISM: Artificial Sequence
<220> FEATURE:
<223> OTHER INFORMATION: SEQLvSDF
<220> FEATURE:
<221> NAME/KEY: misc_feature
<222> LOCATION: (120)..(120)
<223> OTHER INFORMATION: n is g or c

<400> SEQUENCE: 3
ccagacagaa atgatctcct ttgacagaac cggtgacata ttgtacttga gataaaccac        60
atataaatca gtaaaccccg agggcaagta caaatttagt ttaagacaat gattttgaan       120
tgtgaaaatg caaacgaaac cgcgggattc gtctaattcg ccaattacgg ctcagctaac       180
gaggtagcgc taaagcgcac tataacaatc tacagacctt tcgactccag cactttcaga       240
tgtatttcga atcgtgtaca cattaccgga aggcgaatgg aaatgaggtt attatttttg       300
ttacatcatt ttcaagatgg ctggctttgt tgaacatcgg caagaatatt gtgaggtctc       360
cgactccact cccccggggg ccctcctcca tcctgcacca cgcccccttgc cttctccctc       420

```
cottattctc ctccttaccc ttgtttctct taggcttccc ccacggtttc tttcgttaac    480
tcttatctat cctgctttcc tcttttcttt tct                                 513

<210> SEQ ID NO 4
<211> LENGTH: 513
<212> TYPE: DNA
<213> ORGANISM: Artificial Sequence
<220> FEATURE:
<223> OTHER INFORMATION: SEQLvSDM

<400> SEQUENCE: 4
ccagacagaa atgatctcct ttgacagaac cggtgacata ttgtacttga gataaaccac    60
atataaatca gtaaaccccg agggcaagta caaatttagt ttaagacaat gattttgaac   120
tgtgaaaatg caaacgaaac cgcgggattc gtctaattcg ccaattacgg ctcagctaac   180
gaggtagcgc taaagcgcac tataacaatc tacagacctt tcgactccag cactttcaga   240
tgtatttcga atcgtgtaca cattaccgga aggcgaatgg aaatgaggtt attatttttg   300
ttacatcatt ttcaagatgg ctggctttgt tgaacatcgg caagaatatt gtgaggtctc   360
cgactccact cccccggggg ccctcctcca tcctgcacca cgcccttgc cttctccctc    420 ccttattctc ctccttaccc ttgtttctct taggcttccc ccacggtttc tttcgttaac   480
tcttatctat cctgctttcc tcttttcttt tct                                513
```

DNA PROBE SEQUENCE FOR GENETIC SEX IDENTIFICATION OF *LITOPENAEUS VANNAMEI* AND ACQUISITION METHOD

TECHNICAL FIELD

The present invention relates to the prawn sex identification and sex control technology in the aquaculture biotechnology, and particularly to a DNA sequence for genetic sex identification of *Litopenaeus vannamei* and its acquired method.

BACKGROUND

*L. vannamei* is the species which has been farmed most productively among all penaeidae shrimp in China or even in the world. At present, the world average annual output is more than 3,000 thousand tonnes. Like other prawn species, *L. vannamei* has significant difference between female and male individuals in size. The growth rate of female individuals at the middle and later stage is far higher than that of male individuals. Thus, the mono-sex control of *L. vannamei* is useful in order to culture a mono-sex population, thereby having important significance to increase the output and benefit of the prawn culture industry.

Identification of the genetic sex of an individual is the basis for realizing the culture of a mono-sex population of *L. vannamei*. Though the sexes of female and male shrimp can be identified through the morphological external sex characters when shrimps grown to a certain stage. In scientific research and actual production, if early identification of sexes can be realized by a molecular method at the juvenile stage, experiments and culture can be undertaken specifically to individuals of a certain sex, so that the efficiency of the scientific research and actual production can be greatly improved.

In the research of sex markers for prawns, there were already some reports of sex marker screening, for example, Staelens et al. (Staelens, J Rombaut, D., Vercauteren, I., Argue, B., Benzie, J. and Vuylsteke, M. High-density linkage maps and sex-linked markers for the black tiger shrimp (*Penaeus monodon*). Genetics, 2008, 179(2): 917-925.) constructed a high-density genetic linkage map for *P. monodon*, and found two sex difference markers in the genetic linkage map. It was validated that the markers could be used as markers for sex identification in a population of *P. monodon* from other genetic sources. Moreover, the team also applied for a relevant patent (Chinese invention patent No. 200780015173.9, entitled "Sex-Specific Markers for Shrimps and Prawns"). However, the markers could not be used for the sex identification of *L. vannamei* due to the difference between prawn species. In the study of *L. vannamei*, Zhang et al. (Zhang, L., Yang C., Zhang, Y, Li, L., Zhang, X., Zhang, Q., Xiang, J. A genetic linkage map of Pacific white shrimp (*Litopenaeus vannamei*): sex-linked microsatellite markers and high recombination rates. Genetica, 2006, 131(1): 37-49) screened a sex-specific microsatellite site of *L. vannamei* by means of a QTL mapping method. However, it was validated that the microsatellite marker was family specific and could not be used as a marker for sex identification in other sourced population. Similarly, Alcivar-Warren et al. (Alcivar-Warren, A., Meehan-Meola, D., Park, S. W., Xu, Z., Delaney, M., Zuniga, G. Shrimp Map: A low-density, microsatellite-based linkage map of the pacific white leg shrimp, *L. vannamei*: Identification of sex-linked markers in linkage group 4. Journal of Shellfish Research, 2007, 26(4): 1259-1277) also found sex-specific microsatellite markers of *L. vannamei*, but the markers were only restricted to the researched population. In the research of *Fenneropenaeus chinensis*, though more linkage maps were constructed, no corresponding sex identification markers were reported (Li, Z. X., Li, J., Wang, Q., He, Y., Liu, P. AFLP-based genetic linkage map of marine shrimp *Penaeus* (*Fenneropenaeus*) *chinensis*. Aquaculture, 2006, 261(2): 463-472; Sun, Z. N., Liu, P., Li, J., Meng, X., Zhang, X. Construction of a genetic linkage map in *F. chinensis* (Osbeck) using RAPD and SSR markers. Hydrobiologia, 2008, 596: 133-141; Liu, B., Wang, Q., Li, J., Liu, P., He, Y A genetic linkage map of marine shrimp *Penaeus* (*Fenneropenaeus*) *chinensis* based on AFLP, SSR, and RAPD markers. Chinese Journal of Oceanology and Limnology, 2010, 28(4): 815-825.). By means of gene differential expression analysis, one gene showed differential expression between female and male of *F. chinensis* was screened out (Li, S., Li, F., Xie, Y, Wang, B., Wen, R., Zhang, C., Yu, K., Xiang, J. Screening of Genes Specifically Expressed in Males of *F. chinensis* and Their Potential as Sex Markers. Journal of Marine Biology, 2013, 1-9.), and the marker was developed as a marker for female and male sex identification (Chinese invention patent, No. 101709332A). However, so far, no markers for sex identification of *L. vannamei* have been reported.

SUMMARY OF THE INVENTION

The object of the present invention is to provide a DNA sequence for genetic sex identification of *L. vannamei* and its acquired method. The method is not limited by the development stage, individual size and other factors of *L. vannamei*. Even at the larva or juvenile stage, sexes can be accurately identified as long as a certain amount of DNA is available. In addition, the acquired method referred in this patent is also suitable for screening sex difference sequences for other prawn species. A technical means is provided for prawn sex control, mono-sex seed rearing and sex-determining gene screening.

To achieve the above object, the present invention adopts the following solution:

First, the DNA of 1 female parent individual and 50 corresponding female progeny individuals, 1 male parent individual and 50 corresponding male progeny individuals is extracted. High-throughput sequencing is then conducted on the male parent, female parent, pool of 50 female progeny and pool of 50 male progeny individuals using a high-throughput sequencing method. DNA sequences having significant difference in the female and male individuals are analyzed using a bioinformatic method, the obtained differential sequences are verified in the other originated populations. As a result, a DNA sequence for genetic sex identification of *L. vannamei* acquired.

The method for extracting the genomic DNA of *L. vannamei* was conducted following the description in the TIANGEN plant Genomic DNA extraction kit.

The concentration of the DNA of each of the above-mentioned individuals is measured using Nanodrop1000 (USA), and each DNA of the measured individuals is diluted to 100 ng/μl.

An Illumina Hiseq2500 sequencing platform is used in the high-throughput sequencing procedure, and the library construction and the high-throughput sequencing method are conducted in accordance with a standard flow.

The sequencing data of male parent, female parent and progeny individuals were analyzed using bioinformatics method, a mixing pool of female individuals is constructed using the sequencing data of female parent and female progeny individuals, and a mixing pool of male individuals is constructed using the sequencing data of male parent and male progeny individuals. Sequences showing significant difference in depth between the mixing pool of male and female individuals are identified.

A total of 16 sequences showing significant difference between the mixing pools of female and male individuals are found by bioinformatic analysis, and the above-mentioned 16 sequences are amplified using primers designed by Primer 3 Plus on-line design software (http://primer3plus.com/cgi-bin/dev/primer3plus.cgi).

A total of 16 female and 16 male shrimp from different sources are selected, the above-mentioned 16 sequences are amplified using the designed PCR primers. The amplified sequence of each individual are analyzed. As a result, one DNA sequence showing significant difference between the acquired female and male individuals, where the sequence in the female individuals is SEQLvSDF, and the sequence in the male individuals is SEQLvSDM, the different site of the two sequences locates at 120 bp position, the female individual is G/C heterozygote, and the male individual is C homozygote. The primer for amplifying this sequence is:

SEQ ID No.: 1
LvSDPF:
CCAGACAGAAATGATCTCCTTTGA,

SEQ ID No.: 2
LvSDPR:
AGAAAAGAAAAGAGGAAAGCAGGA,

The further analysis is conducted to verify whether the above-mentioned sex marker could be applicable in other sourced populations. A total of 80 female shrimps and 80 male shrimps are analyzed using the above-mentioned primer. It includes 20 female and 20 male individuals purchased from a market randomly, 20 female and 20 male individuals from different families bred in center of Hainan Guangtai Marine Breeding Corporation, 20 female and 20 male individuals from Kona Bay Marine Resources imported in 2012, 20 female and 20 male individuals from Shrimp Improvement System imported in 2014. The amplified sequence is sequenced by a Sanger sequencing method. The result verifies that the sequence indeed shows the difference between female and male, wherein the female individual, the sequence is:
(1) Sequence features:
Genome Sequence: base pair; type: nucleotide; chain type: double chain; topology: linear
(2) Molecular type: DNA
(3) Assumed: No
(4) Antisense: No SEQ ID No.: 3
SEQLvSDF:
CCAGACAGAAATGATCTCCTTTGACAGAACCGGTGACATATTGTACTTGA

GATAAACCACATATAAATCAGTAAACCCCGAGGGCAAGTACAAATTTAGT

TTAAGACAATGATTTTGAA[G/C]TGTGAAAATGCAAACGAAACCGCGGG

ATTCGTCTAATTCGCCAATTACGGCTCAGCTAACGAGGTAGCGCTAAAGC

GCACTATAACAATCTACAGACCTTTCGACTCCAGCACTTTCAGATGTATT

TCGAATCGTGTACACATTACCGGAAGGCGAATGGAAATGAGGTTATTATT

TTTGTTACATCATTTTCAAGATGGCTGGCTTTGTTGAACATCGGCAAGAA

TATTGTGAGGTCTCCGACTCCACTCCCCCGGGGGCCCTCCTCCATCCTGC

ACCACGCCCCTTGCCTTCTCCCTCCCTTATTCTCCTCCTTACCCTTGTTT

CTCTTAGGCTTCCCCCACGGTTTCTTTCGTTAACTCTTATCTATCCTGCT

TTCCTCTTTTCTTTTCT, and in the female individual, the sequence is:
(1) Sequence features:
Genome sequence: base pair; type: nucleotide; chain type: double chain; topology: linear
(2) Molecular Type: DNA
(3) Assumed: No
(4) Antisense: No SEQ ID No.: 4
SEQLvSDM:
CCAGACAGAAATGATCTCCTTTGACAGAACCGGTGACATATTGTACTTGA

GATAAACCACATATAAATCAGTAAACCCCGAGGGCAAGTACAAATTTAGT

TTAAGACAATGATTTTGAACTGTGAAAATGCAAACGAAACCGCGGGATTC

GTCTAATTCGCCAATTACGGCTCAGCTAACGAGGTAGCGCTAAAGCGCAC

TATAACAATCTACAGACCTTTCGACTCCAGCACTTTCAGATGTATTTCGA

ATCGTGTACACATTACCGGAAGGCGAATGGAAATGAGGTTATTATTTTTG

TTACATCATTTTCAAGATGGCTGGCTTTGTTGAACATCGGCAAGAATATT

GTGAGGTCTCCGACTCCACTCCCCGGGGGCCCTCCTCCATCCTGCACCA

CGCCCCTTGCCTTCTCCCTCCCTTATTCTCCTCCTTACCCTTGTTTCTCT

TAGGCTTCCCCCACGGTTTCTTTCGTTAACTCTTATCTATCCTGCTTTCC

TCTTTTCTTTTCT.

The genetic sex of *L. vannamei* could be identified according to the sequence information obtained by sequencing.

The present invention has the following advantages:
1 A DNA sequence for sex identification of *L. vannamei* is obtained so that the genetic sex identification of *Litopenaeus vannamei* can be realized. The method is not limited by the development stage, individual size and other factors of *L. vannamei*, and is a method for conducting genetic sex identification accurately.
2 The sex identification is conducted by a sequencing method, thereby accuracy is very high.
3 By means of the molecular marker, identification of sexes can be realized using only a little of tissue, and can be realized even for frozen and alcohol-soaked tissue.
4 The acquired method for a DNA sequence for sex identification can be applied to other prawn species.

DETAILED DESCRIPTION

Embodiment 1

Acquisition method of DNA sequence for genetic sex identification of *L. vannamei*
1 Muscular tissue were taken respectively from the male parent, female parent, 50 female progeny individuals and 50 male progeny individuals from the same family, the muscular tissue were fixed into liquid nitrogen immediately and then stored in a refrigerator of −80° C. for preservation.

2 The DNA of the above-mentioned sample was extracted using TIANGEN plant Genomic DNA extraction kit (TIANGEN, Beijing), referring to description for operation methods. And the extracted DNA concentration was measured using Nanodrop1000 (Thermo, USA).

3 The extracted DNA was diluted to 100 ng/µl respectively and four different libraries were constructed in accordance with a reduced-representation genome library construction method as follows: a male parent library and a female parent library were constructed respectively, and then a female progeny library by mixing the DNA of 50 female individuals, and a male progeny library by mixing the DNA of 50 male individuals were constructed respectively. High-through put sequencing on the above-mentioned four libraries were conducted using Hiseq2500 platform to obtain original sequencing data of the four libraries.

4 The sequencing data obtained were analyzed by bioinformatics method as follows: Denovo assembling was conducted using the original data of male parent and female parent to obtain reduced-representation genome reference sequences. Then the sequencing data of the four libraries were mapped to the reference sequences, and the mapped read number of each reference sequence in the female parent, the pools of female progeny, the male parent and pools of male progeny were calculated. The sequences showing much higher read depth in the female parent and female progeny pool than that in the male parent and male progeny pool were considered as a female-specific candidate sequence, and the sequences showing much higher read depth in male parent and male progeny pool than that of female parent and female progeny pool were considered as a male-specific candidate sequence.

5 A total of 16 sequences showing significant difference between female and male were obtained by bioinformatic analysis. The above-mentioned 16 sequences were amplified using a designed primers designed by of Primer 3 Plus on-line design software (See, e.g., Methods in Molecular Biology, vol. 132: Bioinformatics Methods and Protocols Edited by: S. Misener and A. Krawetz, Humana Press Inc., Totowa, N.J.)

First, 16 female and 16 male shrimp from different sources were selected, the above-mentioned 16 sequences were amplified using the designed PCR primers. The amplified sequence was analyzed in female and male individuals. As a result, one DNA sequence showing significant difference between all the female and male individuals was obtained. The obtained sequence was further verified in another 60 male individuals and 60 female individuals originated from different sources, and it was proved that the sequence was a female and male difference sequence. The primer for amplifying the sequence was:

```
                                          SEQ ID No.: 1
LvSDPF:
CCAGACAGAAATGATCTCCTTTGA,

SEQ ID No.: 2
LvSDPR: AGAAAAGAAAAGAGGAAAGCAGGA,
```

The amplified sequence in the female individual was SEQLvSDF:

```
                                          SEQ ID No.: 3
CCAGACAGAAATGATCTCCTTTGACAGAACCGGTGACATATTGTACTTGA
GATAAACCACATATAAATCAGTAAACCCCGAGGGCAAGTACAAATTTAGT
TTAAGACAATGATTTTGAA[G/C]GTGAAAATGCAAACGAAACCGCGGGA
TTCGTCTAATTCGCCAATTACGGCTCAGCTAACGAGGTAGCGCTAAAGCG
CACTATAACAATCTACAGACCTTTCGACTCCAGCACTTTCAGATGTATTT
CGAATCGTGTACACATTACCGGAAGGCGAATGGAAATGAGGTTATTATTT
TTGTTACATCATTTTCAAGATGGCTGGCTTTGTTGAACATCGGCAAGAAT
ATTGTGAGGTCTCCGACTCCACTCCCCCGGGGGCCCTCCTCCATCCTGCA
CCACGCCCCTTGCCTTCTCCCTCCCTTATTCTCCTCCTTACCCTTGTTTC
TCTTAGGCTTCCCCCACGGTTTCTTTCGTTAACTCTTATCTATCCTGCTT
TCCTCTTTTCTTTTCT,
``` and the amplified sequence in the male individual was SEQLvSDM:

```
                                          SEQ ID No.: 4
CCAGACAGAAATGATCTCCTTTGACAGAACCGGTGACATATTGTACTTGA
GATAAACCACATATAAATCAGTAAACCCCGAGGGCAAGTACAAATTTAGT
TTAAGACAATGATTTTGAACTGTGAAAATGCAAACGAAACCGCGGGATTC
GTCTAATTCGCCAATTACGGCTCAGCTAACGAGGTAGCGCTAAAGCGCAC
TATAACAATCTACAGACCTTTCGACTCCAGCACTTTCAGATGTATTTCGA
ATCGTGTACACATTACCGGAAGGCGAATGGAAATGAGGTTATTATTTTTG
TTACATCATTTTCAAGATGGCTGGCTTTGTTGAACATCGGCAAGAATATT
GTGAGGTCTCCGACTCCACTCCCCGGGGGCCCTCCTCCATCCTGCACCA
CGCCCCTTGCCTTCTCCCTCCCTTATTCTCCTCCTTACCCTTGTTTCTCT
TAGGCTTCCCCCACGGTTTCTTTCGTTAACTCTTATCTATCCTGCTTTCC
TCTTTTCTTTTCT.
```

Embodiment 2: Molecular Method for Genetic Sexual Identification of *L. vannamei*

In September 2013, a total of 60 *L. vannamei* were randomly selected from aquatic market in Qingdao, and then were delivered to the aquarium building in Institute of Oceanology, Chinese Academy of Sciences for temporary rearing. The muscular tissue were taken out and stored in a refrigerator of −80° C. for frozen preservation.

1. The DNA of the above-mentioned sample were extracted using a Tiangen plant Genomic DNA extraction kit referring to the description of operation methods. The extracted DNA concentration was measured using Nanodrop1000 (Thermo, USA).

2. PCR amplification was conducted on the extracted DNA using the following amplification primer:

```
                                          SEQ ID No.: 1
LvSDPF: CCAGACAGAAATGATCTCCTTTGA,

SEQ ID No.: 2
LvSDPR: AGAAAAGAAAAGAGGAAAGCAGGA.
```

The amplification system were as follows:

| Template (connection product) | 2 μl |
|---|---|
| LvSDPF (10 pmol/μl) | 0.5 μl |
| LvSDPR (10 pmol/μl) | 0.5 μl |
| ExTaqDNABuffer (MgCl$_2$+) | 2.5 μl |
| dNTP (10 mmol/L) | 0.5 μl |
| Ex Taq DNA polymerase | 0.25 μl |
| Sterile water | 18.75 μl |
| Total volume | 25 μl |

The PCR reaction program comprises: conducting denaturing for 3 min at 94° C., and then following 35 circles of 30s at 94° C., 30s at 53° C., and 30s at 72° C., then with a final extension for 10 min at 72° C.

3. PCR products were electrophoresed by agarose and then DNA was extracted using a TIANGEN gel extraction kit. The amplified sequence was sequenced by ABIPRISMTM3700 Genetic Analyzer using an LvSDF primer.

4. Read the peak diagram document of the sequencing result using Bioedit software to look for the nucleotide at 120 bp position of LvSDF and LvSDM sequence. The individual was judged as female if the position is G/C heterozygote, and the individual was judged as male if the position is C homozygote.

Result:

Among the 60 shrimp individuals, the nucleotide at 120 bp position of LvSDF and LvSDM was G/C heterozygote in 34 individuals, and the corresponding individuals were identified as female. The nucleotide at 120 bp position of LvSDF and LvSDM was C homozygous in 26 individuals and the corresponding individuals were identified as male.

The method of the present invention has the characteristics of high efficiency, accuracy and reliability, and possesses broad application potential in the early sex identification and sex control research of prawns.

We claim:

1. A method for genetic sex identification of *Litopenaeus vannamei* individual, comprising:
   a) extracting DNA from the *Litopenaeus vannamei* individual;
   b) amplifying the extracted DNA with a pair of primers consisting of CCAGACAGAAATGATCTCCTTTGA (SEQ ID NO:1) and AGAAAAGAAAAGAGGAAAGCAGGA (SEQ ID NO:2) to form an amplicon; and
   c) sequencing the amplicon generated by the pair of primers; and
   d) detecting the nucleotides present at position 120 of the amplicon wherein if the nucleotide at position 120 of the amplicon are G/C heterozygote, the individual is a female, and
   wherein if the nucleotides at position 120 of the amplicon is homozygote C/C, the individual is a male.

2. The method of claim 1 wherein the amplicon has a sequence selected from:

CCAGACAGAAATGATCTCCTTTGACAGAACCGGTGACATATTGTACTTGA
GATAAACCACATATAAATCAGTAAACCCCGAGGGCAAGTACAAATTTAGT
TTAAGACAATGATTTTGAA[G/C]TGTGAAAATGCAAACGAAACCGCGGG
ATTCGTCTAATTCGCCAATTACGGCTCAGCTAACGAGGTAGCGCTAAAGC
GCACTATAACAATCTACAGACCTTTCGACTCCAGCACTTTCAGATGTATT
TCGAATCGTGTACACATTACCGGAAGGCGAATGGAAATGAGGTTATTATT
TTTGTTACATCATTTTCAAGATGGCTGGCTTTGTTGAACATCGGCAAGAA
TATTGTGAGGTCTCCGACTCCACTCCCCGGGGGCCCTCCTCCATCCTGC
ACCACGCCCCTTGCCTTCTCCCTCCCTTATTCTCCTCCTTACCCTTGTTT
CTCTTAGGCTTCCCCCACGGTTTCTTTCGTTAACTCTTATCTATCCTGCT
TTCCTCTTTTCTTTTCT or

CCAGACAGAAATGATCTCCTTTGACAGAACCGGTGACATATTGTACTTGA
GATAAACCACATATAAATCAGTAAACCCCGAGGGCAAGTACAAATTTAGT
TTAAGACAATGATTTTGAACTGTGAAAATGCAAACGAAACCGCGGGATTC
GTCTAATTCGCCAATTACGGCTCAGCTAACGAGGTAGCGCTAAAGCGCAC
TATAACAATCTACAGACCTTTCGACTCCAGCACTTTCAGATGTATTTCGA
ATCGTGTACACATTACCGGAAGGCGAATGGAAATGAGGTTATTATTTTTG
TTACATCATTTTCAAGATGGCTGGCTTTGTTGAACATCGGCAAGAATATT
GTGAGGTCTCCGACTCCACTCCCCGGGGGCCCTCCTCCATCCTGCACCA
CGCCCCTTGCCTTCTCCCTCCCTTATTCTCCTCCTTACCCTTGTTTCTCT
TAGGCTTCCCCCACGGTTTCTTTCGTTAACTCTTATCTATCCTGCTTTCC
TCTTTTCTTTTCT.

3. A method for genetic sex identification of a *Litopenaeus vannamei* individual comprising:
   a) extracting DNA from the *Litopenaeus vannamei* individual,
   b) amplifying the extracted DNA with a pair of primers to form an amplicon having a sequence selected from:

SEQLvSDF:
CCAGACAGAAATGATCTCCTTTGACAGAACCGGTGACATATTGTACTTGA
GATAAACCACATATAAATCAGTAAACCCCGAGGGCAAGTACAAATTTAGT

```
TTAAGACAATGATTTTGAA[G/C]TGTGAAAATGCAAACGAAACCGCGGG

ATTCGTCTAATTCGCCAATTACGGCTCAGCTAACGAGGTAGCGCTAAAGC

GCACTATAACAATCTACAGACCTTTCGACTCCAGCACTTTCAGATGTATT

TCGAATCGTGTACACATTACCGGAAGGCGAATGGAAATGAGGTTATTATT

TTTGTTACATCATTTTCAAGATGGCTGGCTTTGTTGAACATCGGCAAGAA

TATTGTGAGGTCTCCGACTCCACTCCCCGGGGGCCCTCCTCCATCCTGC

ACCACGCCCCTTGCCTTCTCCCTCCCTTATTCTCCTCCTTACCCTTGTTT

CTCTTAGGCTTCCCCCACGGTTTCTTTCGTTAACTCTTATCTATCCTGCT

TTCCTCTTTTCTTTTCT;
``` or

```
SEQLvSDM:
CCAGACAGAAATGATCTCCTTTGACAGAACCGGTGACATATTGTACTTGA

GATAAACCACATATAAATCAGTAAACCCCGAGGGCAAGTACAAATTTAGT

TTAAGACAATGATTTTGAACTGTGAAAATGCAAACGAAACCGCGGGATTC

GTCTAATTCGCCAATTACGGCTCAGCTAACGAGGTAGCGCTAAAGCGCAC

TATAACAATCTACAGACCTTTCGACTCCAGCACTTTCAGATGTATTTCGA

ATCGTGTACACATTACCGGAAGGCGAATGGAAATGAGGTTATTATTTTTG

TTACATCATTTTCAAGATGGCTGGCTTTGTTGAACATCGGCAAGAATATT

GTGAGGTCTCCGACTCCACTCCCCGGGGCCCTCCTCCATCCTGCACCA

CGCCCCTTGCCTTCTCCCTCCCTTATTCTCCTCCTTACCCTTGTTTCTCT

TAGGCTTCCCCCACGGTTTCTTTCGTTAACTCTTATCTATCCTGCTTTCC

TCTTTTCTTTTCT;
``` and c) determining the nucleotide at position 120 of the amplicon, wherein the presence of a G/C heterozygote at position 120 indicates a female individual or the presence of a C/C homozygote indicates the individual is a male.

4. The method of claim 3 wherein the amplicon is

```
                                        (SEQ ID NO: 3)
CCAGACAGAAATGATCTCCTTTGACAGAACCGGTGACATATTGTACTTGA

GATAAACCACATATAAATCAGTAAACCCCGAGGGCAAGTACAAATTTAGT

TTAAGACAATGATTTTGAA[G/C]TGTGAAAATGCAAACGAAACCGCGGG

ATTCGTCTAATTCGCCAATTACGGCTCAGCTAACGAGGTAGCGCTAAAGC

GCACTATAACAATCTACAGACCTTTCGACTCCAGCACTTTCAGATGTATT

TCGAATCGTGTACACTTACCGGAAGGCGAATGGAAATGAGGTTATTATTT

TTGTTACATCATTTTCAAGATGGCTGGCTTTGTTGAACATCGGCAAGAAT

ATTGTGAGGTCTCCGACTCCACTCCCCGGGGCCCTCCTCCATCCTGCA

CCACGCCCCTTGCCTTCTCCCTCCCTTATTCTCCTCCTTACCCTTGTTTC

TCTTAGGCTTCCCCCACGGTTTCTTTCGTTAACTCTTATCTATCCTGCTT

TCCTCTTTTCTTTTCT.
```

5. The method of claim 3 wherein the amplicon is

```
                                        (SEQ ID NO: 4)
CCAGACAGAAATGATCTCCTTTGACAGAACCGGTGACATATTGTACTTGA

GATAAACCACATATAAATCAGTAAACCCCGAGGGCAAGTACAAATTTAGT

TTAAGACAATGATTTTGAACTGTGAAAATGCAAACGAAACCGCGGGATTC

GTCTAATTCGCCAATTACGGCTCAGCTAACGAGGTAGCGCTAAAGCGCAC

TATAACAATCTACAGACCTTTCGACTCCAGCACTTTCAGATGTATTTCGA

ATCGTGTACACATTACCGGAAGGCGAATGGAAATGAGGTTATTATTTTTG

TTACATCATTTTCAAGATGGCTGGCTTTGTTGAACATCGGCAAGAATATT

GTGAGGTCTCCGACTCCACTCCCCGGGGCCCTCCTCCATCCTGCACCA

CGCCCCTTGCCTTCTCCCTCCCTTATTCTCCTCCTTACCCTTGTTTCTCT

TAGGCTTCCCCCACGGTTTCTTTCGTTAACTCTTATCTATCCTGCTTTCC

TCTTTTCTTTTCT.
```

\* \* \* \* \*